United States Patent [19]
Honeycutt

[11] Patent Number: 4,816,307
[45] Date of Patent: Mar. 28, 1989

[54] NOVEL INFECTIOUS WASTE CONTAINMENT

[76] Inventor: Travis W. Honeycutt, 8 Lago Sud, Irvine, Calif. 92715

[21] Appl. No.: 4,593

[22] Filed: Jan. 20, 1987

[51] Int. Cl.⁴ ............................................. B65D 85/24
[52] U.S. Cl. .................................. 428/34.1; 206/366; 206/526; 264/279.1; 428/35.7
[58] Field of Search ..................... 206/524.5, 366, 570, 206/571; 428/35; 156/298; 264/279.1; 220/1 T

[56] References Cited

U.S. PATENT DOCUMENTS

| | | | |
|---|---|---|---|
| 3,292,776 | 12/1966 | Penn | 206/366 X |
| 3,638,709 | 2/1972 | Brown, Jr. et al. | 264/279.1 X |
| 3,653,567 | 4/1972 | Selvaggio | 206/570 X |
| 3,897,579 | 7/1975 | Weinstein | 428/179 X |
| 3,921,801 | 11/1975 | Sway | 206/575 |
| 3,999,653 | 12/1976 | Haigh et al. | 206/524.5 X |
| 4,134,929 | 1/1979 | Stoakley et al. | 525/305 X |
| 4,139,693 | 2/1979 | Schoenberg | 428/442 X |
| 4,170,585 | 10/1979 | Motegi et al. | 526/298 X |
| 4,171,416 | 10/1979 | Motegi et al. | 526/298 X |
| 4,320,157 | 3/1982 | von Hagens | 428/13 |
| 4,410,086 | 10/1983 | Simpson | 206/366 |
| 4,444,933 | 4/1984 | Columbus et al. | 525/295 X |
| 4,477,607 | 10/1984 | Litke | 525/259 X |
| 4,520,926 | 6/1985 | Nelson | 206/366 |
| 4,600,112 | 7/1986 | Shillington et al. | 206/366 X |
| 4,650,086 | 3/1987 | Morrison, Jr. | 206/524.5 X |
| 4,662,516 | 5/1987 | Baker, Sr. et al. | 206/366 X |
| 4,715,498 | 12/1987 | Hanifl | 206/366 |
| 4,722,472 | 2/1988 | Bruno | 206/366 X |
| 4,759,445 | 7/1988 | McVay | 206/524.5 X |

OTHER PUBLICATIONS

Article: "Infection Prevention Products", published in Biomedical Business International, vol. IX, No. 13, Jul. 10, 1986, pp. 128 & 129.

*Primary Examiner*—Henry F. Epstein
*Attorney, Agent, or Firm*—Limbach, Limbach & Sutton

[57] ABSTRACT

A kit and method for its use for containing potentially infectious devices. The potentially infectious devices are deposited in a container to which is added a cyanoacrylate ester monomer-containing composition to at least partially envelope the potentially infectious devices. The cyanoacrylate ester monomer-containing composition is caused to harden through polymerization of the cyanoacrylate ester monomer to immobilize the devices.

19 Claims, 1 Drawing Sheet

U.S. Patent   Mar. 28, 1989   4,816,307
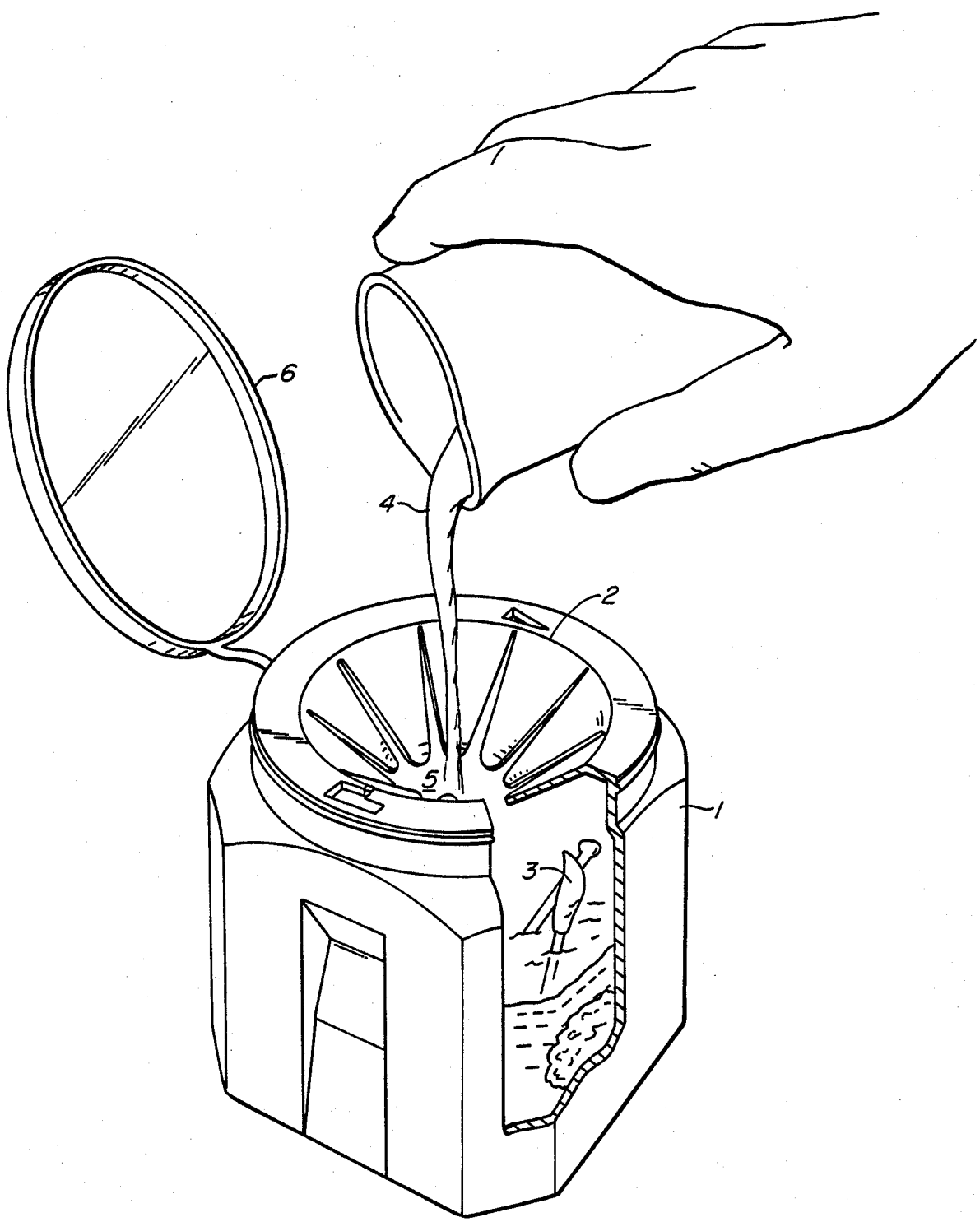
FIGURE

NOVEL INFECTIOUS WASTE CONTAINMENT

BACKGROUND OF THE INVENTION

In hospitals, clinics and other environments in which ill patients are routinely examined and treated, medical practitioners contaminate a host of devices such as needles, syringes, tubing, and scalpels with boood and other bodily fluids. This is often done when feeding patients, drawing blood, vaccinating and otherwise inoculating. Quite often, patients' bodily fluids are infected with pathogenic bacteria, viruses, fungi and other matter. This potential source of pathogenicity has become acute with the knowledge and identification of certain pathogens such a hepatitis B and the AIDS virus, among other deadly and infectious materials.

These pathogenetic materials are potentially a source of infection for doctors, nurses, aides, orderlies, technicians, and even to visitors to the hospital or clinic, as well as to the patients themselves. The various devices infected must thus be contained and/or destroyed.

Currently, infectious waste, called "sharps", is generally disposed of by insertion of the infected material into a hard plastic container. These containers are then removed by housekeeping personnel and sent to a site for bagging and storage. After bagging, the containers are often stored or removed to yet another site for sterilization. Even when closed, locked and bagged, the containers are not airtight, and thus can potentially spill and contaminate the atmosphere. Handling of the waste containers by housekeeping personnel often results in infected needles penetrating the storage containers, thus providing a potentially dangerous condition for housekeeping personnel.

Following sterilization, the contaminated material is often removed to another location for incineration. After sterilization, the contaminated waste disposal containers resemble, and are often referred to as, "porcupines" because the often used plastic containers shrink around the needle and other devices when heated in an autoclave or similar device, resulting in needle exposure through the sides of the containers. In this condition, the containers are indeed quite dangerous to handle, whether or not they remain the housing for infectious devices.

In addition to the above-recited difficulties, current state of the art disposal techniques are further flawed in the use of so-called "anti-removal" or anti-theft"containers. Infectious devices are often put into plastic containers which contain guards for preventing needle retrieval. However, it is relatively easy to reach into such a container and retrieve the "sharps". As such, current disposal methods do not render the needles and sharps irretrievable and unstable at the point of disposal.

One of the most serious deficiencies with current disposal methods is that they do not prevent the aerosoling or spilling of infectious materials into the ambient atmosphere, thus potentially causing the spread of infectious germs, bacteria, fungi and viral fragments. Current containers are not air-tight, even when they are eventually closed and locked.

It is thus an object of the present invention to provide a superior method for containing potential infectious devices which overcomes the difficulties recited above.

BRIEF DESCRIPTION OF THE DRAWING

This and further objects of the present invention will be more fully appreciated when considering the following disclosure and appended drawing wherein:

The FIGURE depicts a perspective view of a container and prescribed method for practicing the present invention.

SUMMARY OF THE INVENTION

In its broadest sense, the present invention is a method for containing potentially infectious devices. The method comprises depositing the potentially infectious devices in a container to which is added a sufficient quantity of a cyanoacrylate ester monomer-containing composition. The composition is added to the container to at least partially envelope the potentially infectious devices. The cyanoacrylate ester monomer-containing composition is then hardened through polymerization of the cyanoacrylate ester monomer to immobilize the potentially infectious devices.

DETAILED DESCRIPTION OF THE INVENTION

The present method involves the entrapment, anchoring and fuming or precipitation of contaminated and/or infected "sharps" and their aerosol through the use of a container and solidifying agent at the point of disposal. The container is first filled by hospital personnel with the infected "sharps" material, and then is contained by a liquid which turns into a solid block of plastic with associated fuming and surface coating within a short period after the liquid is poured over the sharps or infectious devices. The liquid and fume contains biocides and produces biocidal activity and sanitizing heat during the course of the reaction, which is decidedly exothermic. The solidifying liquid is a cyanoacrylate ester monomer-containing composition, which acts as a fumer and lacrimator. Such materials precipitate from their fumes in the presence of water and proteins which are known constituents of blood and bodily fluids, thus immobilizing and containing these fluids. As such, $\alpha$-cyanoacrylate ester monomer-containing compositions provide an ideal material to contain potentially infectious devices which have been infected with bodily fluids.

Turning to the figure container 1 which represents a commercially available well-known "sharps" containment device is provided with baffles 2 which facilitate the disposal of sharps 3, but which make it difficult for the removal of such devices. However, as noted previously, removal is not impossible, and the mere inversion of container 1 with sufficient agitation will result in at least some of devices 3 falling from the container opening. Once container 1 is filled to the desired level with sharps 3, $\alpha$-cyanoacrylate ester monomer-containing composition 4 can be poured within opening 5, preferably to a level which is sufficient to at least immobilize, and preferably completely immerse, sharps 3. When this is done, lid 6 can be closed over opening 5, which results in the completion of the disposal cycle.

The immobilizing composition comprises an $\alpha$-cyanoacrylate esther monomer having the following structure:

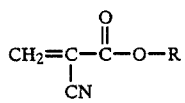

wherein R is a member selected from the group consisting of an alkyl from 1 to 16 carbon atoms, an alkoxyalkyl, such as methoxyethyl or ethoxyethyl, and an aromatic, such as cyclohexyl and/or substitutes thereof. Most preferred are the 1 to 4 carbon atom esters such as methyl, ethyl, propyl, isopropyl, n-butyl, and isobutyl.

As α-cyanoacrylates can polymerize via the free radical route, to enhance shelf life, it is preferable that a free radical scavenger be included in the composition. Such scavengers include hydroquinone, monoethyl ether of hydroquinone, butylated hydroxyanisole, butylated hydroxytoluene, and t-butyl hydroquinone. Hydroquinone is the preferred free radical scavenger for use herein.

To further enhance the stability of the composition, a stabilizer is optionally included. Suitable stabilizers for practicing the present invention comprise one or more members selected from the group consisting of sulphur dioxide, hydrogen fluoride, nitrogen oxide, phosphoric acid, phosphorous acid, boric trifluoride, stannic chloride, ferric chloride, sultones, and aromatic sulfonic acids. These materials are included in amounts from approximately 2 to 5000 ppm, more often from 10 to 500 ppm, and most preferably from 20 to 400 ppm.

It is further often useful that a plasticizer be employed in this composition. Plasticizers for use herein comprise one or more members selected from the group consisting of monofunctional aliphatic esters, such as butyl acetate and butyl cyanoacetate, difunctional aliphatic esters, such as dibutylphthalate, phosphate esters and phosphonate esters. Although dibutyl—and dioctylphthalate are preferable in carrying out the present invention, one could use 3,4,5-trihydroxybenzoic acid and its esters, as taught in U.S. Pat. No. 4,139,693, among others known in the trade.

The preferred viscosity of the present composition is that of water, approximately between 0 and 1000 cps when measured on a Brookfield viscometer at 20 rpm with a number 4 spindle. Although the composition can be thixotropic in nature, it is preferable to not employ a highly viscous material to ensure that the cyanoacrylate ester monomer-containing composition has the desirable "penetrating" effect to insure complete coverage over all utensils found within the container. If viscosity is to be increased, viscosity enhancers, such as Cabosil ® NTS, as taught in U.S. Pat. No. 4,477,607, may be employed, which is a hydrophobic fumed silica treated with polydimethylsiloxane. One could also employ PMMA, PECA, and PEMA, as well as cellulose esters. If any of these materials are employed, they should be thoroughly dry, free of any Lewis base, and of a neutral or slightly acidic pH.

It is further contemplated that in practicing the present invention, an activating agent or catalyst be employed to promote the polymerization of the cyanoacrylate ester monomer. Preferably, the catalyst consists of a primary, secondary or tertiary amine or any other suitable Lewis base material when taken alone, or in a solvent or plasticizer such as a detergent, soap, surfactant, alkaloid or base. Suitable bases include sodium hydroxide, sodium carbonate, and so forth.

The catalyst can be deposited on the inside of container 1 or in a paper or sponge material which can be placed in the container to provide a concentration from approximately 0.00001% to 5% of the effective volume of the container. A suitable solvent for the activating agent can be water, while dioctylphthalate can be employed as a suitable plasticizer.

Example

An eight-ounce container blow-molded from high density polyethylene was fitted with anti-retrieval fingers (element 2 of the figure) and with a screw or snap lid (element 6 of the figure). The inside of the container was coated with one gram of polyethylene amine that was blended with one gram of triallylcyanurate and 10 grams of dioctylphthalate. The container was fitted with contaminated syringes that were previously used for intramuscular injection and venous blood withdrawal. After the container was "filled" with the contaminated syringes, there was sufficient void space for introduction of the immobilizing liquid to intermingle and fill the container. As such, the container was then filled to the finger guard level with the solidifying composition, which was composed of 50% ethyl α-cyanoacrylate resin available from Loctite Corporation and 50% dioctylphthalate available from Eastman Kodak, sold under the trademark Kodaflex DOP ®. This mixture was inhibited with 5000 ppm hydroquinone and stabilized with 25 ppm sulphur dioxide gas and 100 ppm trichloroacetic acid.

The container was then closed with a snap cap and turned upside down and shaken vigorously for two minutes. The container was allowed to sit right side up for two hours to allow the solidifying liquid the opportunity to lock on the lid and decontaminate the finger guard area with fuming. As the cyanoacrylate monomer began to polymerize, heat was released from the exothermic reaction, causing a rise in temperature of the container and its contents to the range of approximately 120 to 150° F. As this occurred, a hard, dense block of polyethyl-α-cyanoacrylate plastic formed in the container, which completely locked up and anchored the infected syringes, and prevented their retrieval and or use. Further, the heat of polymerization sanitized the container and formed a surface film in the voids.

As the container began to cool down, it could be handled as ordinary sanitary trash.

Treatment of contaminated syringes and other similar objects with the above-described invention obviates the necessity to engage in arduous and difficult processes of sterilization and incineration, while the solidifying liquid renders the infectious materials non-aerosoling.

I claim:

1. A method for containing potentially infectious devices comprising:
   A. depositing said potentially infectious devices in a container;
   B. adding to said container a sufficient quantity of a cyanoacrylate ester monomer-containing composition to at least partially envelope said potentially infectious devices; and
   C. causing said cyanoacrylate ester monomer-containing composition to harden through polymerization of said cyanoacrylate ester monomer to immobilize said potentially infectious devices.

2. The method of claim 1 further comprising the addition of a catalyst to promote the polymerization of said cyanoacrylate ester monomer.

3. The method of claim 2 wherein said catalyst is coated on one or more of the inner wall of said container prior to the deposit of the potentially infectious devices therein.

4. The method of claim 1 wherein said composition further comprises:
  A. approximately 2 to 10,000 ppm of a stabilizer for the cyanoacrylate ester monomer;
  B. approximately 2 to 5000 pm of an inhibitor for the cyanoacrylate ester monomer; and
  C. approximately 5 to 70% (wt.) of a plasticizer for the cyanoacrylate ester monomer.

5. The method of claim 4 wherein said composition further comprises a viscosity enhancer resulting in a viscosity of the composition to be approximately 0 to 1000 cps when measured on a Brookfield viscometer at 20 rpm with a number 4 spindle.

6. The method of claim 2 wherein said catalyst is present in an amount between approximately .00001 to 5% by volume based upon the volume of the container, said catalyst comprising a member selected from the group consisting of primary, secondary and tertiary amines.

7. The method of claim 4 wherein said stabilizer comprises a hydroquinone.

8. The method of claim 4 wherein said inhibitor is of the Lewis acid type comprising a member selected from the group consisting of $SO_2$, $NO_2$, $CO_2$ and $BF_3$ etherate.

9. The method of claim 4 wherein said plasticizer comprises a member selected from the group consisting of dibutylphthalate, dioctylphthalate, diisononylphthalate, dioctyladipate and triacetin.

10. The method of claim 1 wherein said cyanoacrylate ester monomer-containing composition upon hardening substantially encapsulates, anchors and precipitates said potentially infectious devices within said container.

11. A kit for containing partially infectious devices comprising a container for holding said potentially infectious devices and a sufficient quantity of a cyanoacrylate ester monomer-containing composition to be supplied to said container in an amount to at least partially envelope said potentially infectious devices when added to said container.

12. The kit of claim 11 further comprising a catalyst to promote the polymerization of said cyanoacrylate ester monomer.

13. The kit of claim 12 wherein said catalyst is coated on one or more of the inner walls of said container prior to the deposit of the potentially infectious devices therein.

14. The kit of claim 11 wherein said composition further comprises:
  A. approximately 2 to 10,000 ppm of a stabilizer for the cyanoacrylate ester monomer;
  B. approximately 2 to 5000 pm of an inhibitor for the cyanoacrylate ester monomer; and
  C. approximately 5 to 70% (wt.) of a plasticizer for the cyanoacrylate ester monomer.

15. The kit of claim 14 wherein said composition further comprises a viscosity enhancer resulting in a viscosity of the composition to be approximately 0 to 1000 cps when measured on a Brookfield viscometer at 20 rpm with a number 4 spindle.

16. The kit of claim 12 wherein said catalyst is present in an amount between approximately .00001 to 5% by volume based upon the volume of the container, said catalyst comprising a member selected from the group consisting of primary, secondary and tertiary amines.

17. The kit of claim 14 wherein said stabilizer comprises a hydroquinone.

18. The kit of claim 14 wherein said inhibitor is of the Lewis acid type comprising a member selected from the group consisting of $SO_2$, $NO_2$, $CO_2$ and $BF_3$ etherate.

19. The kit of claim 14 wherein said plasticizer comprises a member selected from the group consisting of dibutylphthalate, dioctylphthalate, diisononylphthalate, dioctyladipate and triacetin.

* * * * *